United States Patent [19]

Hinzmann et al.

[11] 4,321,993
[45] Mar. 30, 1982

[54] ARRANGEMENT FOR ORIENTING AND CONVEYING BARRELS OF TAMPON INSERTERS

[75] Inventors: Alfred Hinzmann; Erich Presser, both of Richmond, Va.

[73] Assignee: Hauni-Richmond, Inc., Richmond, Va.

[21] Appl. No.: 110,606

[22] Filed: Jan. 9, 1980

[51] Int. Cl.³ .............................................. B65G 47/24
[52] U.S. Cl. ................................... 198/400; 198/382; 198/396; 198/445; 198/461; 193/47
[58] Field of Search ................ 198/382, 383, 396, 400, 198/443, 445, 446, 461, 389, 721, 809; 193/47

[56] References Cited

U.S. PATENT DOCUMENTS

| | | | |
|---|---|---|---|
| 1,495,610 | 5/1924 | Paridon | 198/446 |
| 2,377,154 | 5/1945 | Hurley, Jr. | 193/47 |
| 2,592,141 | 4/1952 | Holdren | 198/382 |
| 3,184,035 | 5/1965 | Wiley | 198/383 |
| 3,517,797 | 6/1970 | Daleffe et al. | 198/389 |
| 3,608,972 | 9/1971 | Rudszinat | 198/461 X |
| 3,978,969 | 9/1976 | Williams et al. | 198/461 |

FOREIGN PATENT DOCUMENTS 1039978 10/1953 France .................................. 198/443

*Primary Examiner*—Jeffrey V. Nase
*Attorney, Agent, or Firm*—Peter K. Kontler

[57] ABSTRACT

An arrangement for orienting and conveying barrels of catamenial tampon inserters includes a support which is constituted by a plurality of alternating cylindrical first and second support elements which rotate in opposite directions. Each first support element forms with the associated second support element a receiving channel, and an upper run of a V-belt conveyor is arranged at the bottom of this receiving channel and advances longitudinally of the support elements. The barrels are piled on top of the support elements in a randomly oriented collection, such as a layer or pile, and enter the respective receiving channels only when assuming one of two orientations. The engagement of the lowermost barrel with the external surfaces of the support elements causes the barrel to turn toward a position of parallelism with the axes of the support elements. Those barrels which are carried on top or between the barrels advanced by the V-belt conveyors in the receiving channels are returned into the collection by a refuser arrangement, and a succession of two conveyor pairs the downstream one of which advances at a higher speed than the upstream one disassociates those barrels which may have partially entered one another. A reversing arrangement then causes the barrels to assume only one of the two previously possible orientations.

14 Claims, 12 Drawing Figures

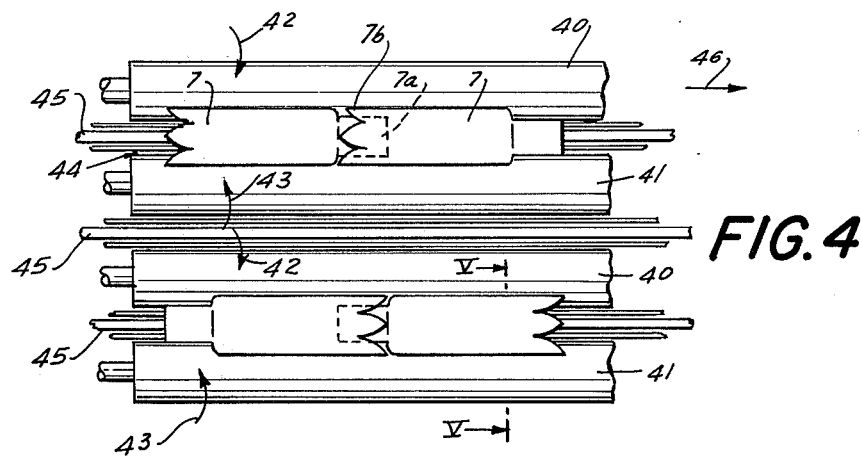
FIG. 4
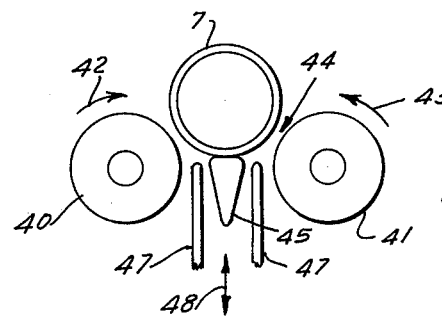
FIG. 5
FIG. 7
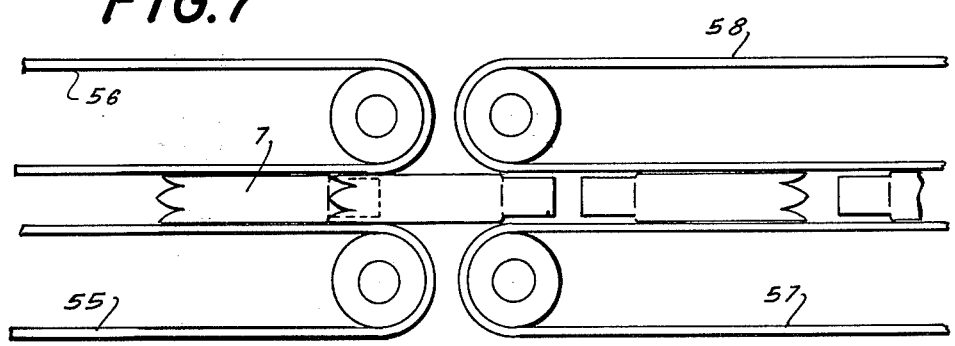
FIG. 6
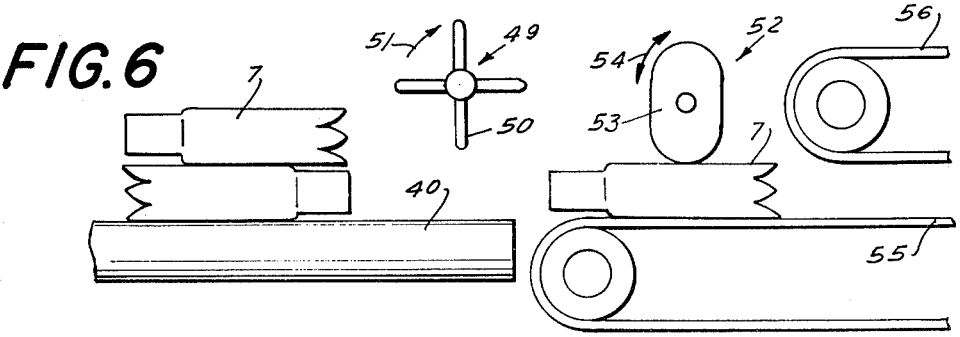

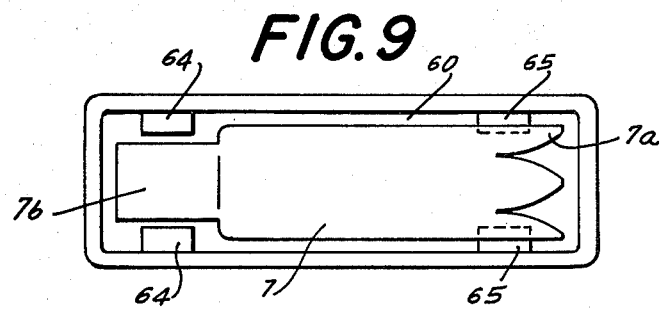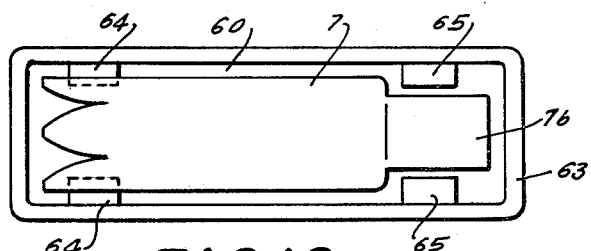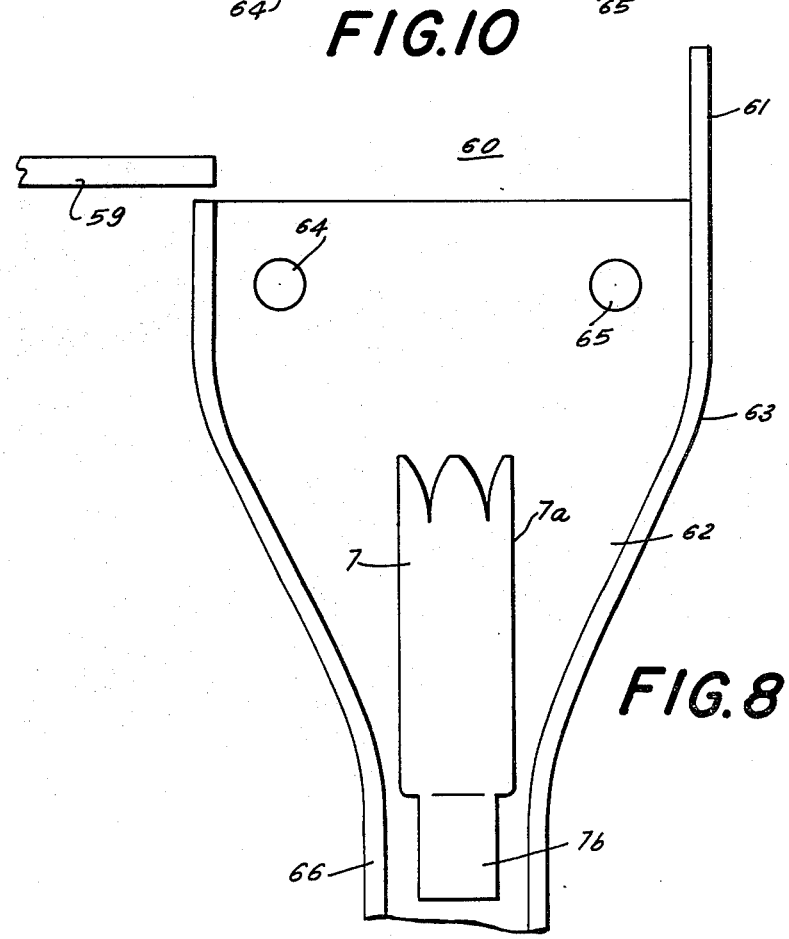

ARRANGEMENT FOR ORIENTING AND CONVEYING BARRELS OF TAMPON INSERTERS

BACKGROUND OF THE INVENTION

The present invention relates to an arrangement for orienting and conveying elongated objects in general, and more particularly to an arrangement for orienting and conveying barrels of tampon inserters.

In recent years, catamenial tampons have been gaining an increasing degree of popularity, especially among active women, as superior and more convenient substitutes for customary sanitary napkins. One reason for this is that they are imperceptible through garments, no matter how tight these garments may be. Another reason may be that, if properly used, they give protection against the soiling of the garment or underwear, which is superior to that afforded by the santiary napkins.

The tampons may be acquired as such, and they may be introduced manually without resorting to the use of any auxiliary devices. However, this method of introduction is yielding, in an ever-increasing manner, to the use of tampon inserters, which are usually constructed as cylinder-and-piston, or telescoping, assemblies, and which are introduced with the respective tampon accommodated therein, whereupon the tampon is expelled therefrom and the empty tampon inserter is withdrawn.

While it is possible to so construct a tampon inserter as to be reuseable over and over again, the current trend is toward the use of disposable tampon inserters which serve as protectors for the tampons during their handling at the manufacturing plant, such as packaging, and during the transportation and handling prior to actual use. After the tampon accommodated in the respective tampon inserter has been expelled therefrom, the tampon inserter is discarded.

For the tampon inserter to be able to act as a protector, and to facilitate the introduction of the tampon inserter, it is already known, for instance, from the U.S. Pat. No. 3,895,634 to give the leading end portion thereof a hemispherical configuration. This reduces if not eliminates the danger of injury and existence of an unpleasant feeling during the introduction.

There are also already known various machines for making the tampons, attaching withdrawal strings thereto, assembling the components of the tampon inserters, introducing the tampons into the tampon inserters, and closing the leading ends of the tampon inserters after the introduction of the tampons thereinto. However, experience has shown that the existing machinery operates at a rather slow pace and in a very cumbersome manner, which increases the manufacturing cost of the final articles both in terms of capital investment and labor costs, which necessarily reflects itself in the price of the final article.

OBJECTS AND SUMMARY OF THE INVENTION

Accordingly, it is the general object of the present invention to avoid the disadvantages of the prior art.

It is an object of the present invention to so construct a machine for making tampon inserter-tampon assemblies as to render it possible to produce such assemblies at a speed which is unknown to and impossible to achieve by any of the existing machinery.

A further object of the present invention is to develop an arrangement for orienting and conveying barrels of tampon inserters which is capable of operating at very high speeds and of meeting demands of a high-speed catamenial tampon/tampon inserter assembly manufacturing apparatus.

Yet another object of the invention is to so design the arrangement of the type here under consideration as to be able to meet all exigencies which could occur during the orientation and conveyance.

A concomitant object of the present invention is to so construct the arrangement of the present invention as to be simple, inexpensive and yet reliable.

One feature of the present invention resides in the provision of an arrangement for orienting and conveying elongated objects, expecially barrels of tampon inserters, which comprises means for supporting a collection of randomly oriented elongated objects, this supporting means including at least a first and a neighboring substantially parallel second support element constituting a cooperating pair, at least the first of the support elements of the pair having a cylindrical engaging surface centered on a longitudinal axis and this support element being mounted for rotating about this longitudinal axis, the support elements, of the pair spaced from one another transversely of the longitudinal axis to define with each other a receiving channel for a succession of the objects which are oriented substantially in parallelism with the longitudinal axis; means for rotating the first support element about the longitudinal axis in frictional engagement of the engaging surface of the first support elements with any improperly oriented objects which are supported thereon, with attendant reorientation of improperly oriented objects toward parallelism with the longitudinal axis and entry into the receiving channel; and conveyor means extending into the receiving channel, advancing in a predetermined direction along the longitudinal axis, and entraining the objects received in the receiving channel for advancement in the predetermined direction. It will be appreciated that, when the arrangement is constructed in the above-mentioned manner, those objects which are located at the bottom of the collection or heap or objects which are oriented in a substantial parallelism with the longitudinal axis will immediately enter the receiving channel and will be conveyed by the conveyor from below the other objects and eventually leave the collection. On the other hand, those objects at the bottom of the heap which initially extend across the receiving space will be turned owing to their engagement with the engaging surface of the rotating support elements until their orientation is changed to that of substantial parallelism with the longitudinal axis, at which time they enter the receiving channel and be advanced by the conveyor in the same as discussed above.

It is particularly advantageous when also the second support element of the pair has a cylindrical engaging surface which is centered on another longitudinal axis that is substantially parallel to the longitudinal axis of the first support element. The second support element is rotated about its longitudinal axis, preferably in a sense opposite to that in which the first support element is rotated. Under these circumstances, the first and second support elements cooperate with one another, so long as the respective object extends across the receiving space therebetween, in turning the latter into substantial parallelism with their longitudinal axes. The two cooperating support elements constructed in this manner can be driven in synchronism with each other (but in opposite senses) by a common drive constituting the rotating means.

According to a currently preferred embodiment of the present invention, the support means includes at least one (but preferably more than one) additional support element which is similar to one of the support elements of the pair and which is located along and in substantial parallelism to the other element of the pair to constitute an additional pair of support elements therewith, such additional pair of support elements defining an additional receiving channel for an additional succession of properly oriented objects. Of course, when this measure is resorted to, there will be provided an additional conveyor means in the additional receiving channel. In this manner, the capacity of the arrangement is doubled (or, generally speaking, raised to a multiple corresponding to the number of the additional support elements) with respect to a situation where only the initial single pair of the support elements is provided.

It is especially advantageous when the conveying means includes at least one belt conveyor (particularly a V-belt conveyor) which has an upper run that extends longitudinally of the receiving channel and engages the object received in the latter from below. This results in a particularly simple construction, and yet the frictional engagement between the upper run of the conveyor and the respective object is more than sufficient to advance the latter in the predetermined direction out of the collection below the other objects of the collection.

Under certain circumstances, particularly when a jam occurs downstream of the above-discussed part of the arrangement, it may be advantageous or even necessary to discontinue the advancement of the objects with the conveyor means. For this reason, the arrangement of the present invention is equipped with appropriate means for achieving this purpose. Such discontinuing means advantageously includes at least one lifting element which is mounted on the supporting means for movement between a retracted position in which it is spaced from the objects received in the receiving channel, and an extended position in which it lifts the objects out of the range of the conveyor means. It is further advantageous when the lifting element is received between one of the support elements and the conveyor means in its extended position, and when the discontinuing means further includes another lifting element similar to and movable together with the one lifting element and received between the conveyor means and the other of the support elements in the extended position thereof. Under these circumstances, all of the objects which would otherwise be entrained by the conveyor means rest on the lifting elements, so that it is not necessary to discontinue the operation of the conveyor means, and yet the supply of further objects to the region at which the jam has occurred is interrupted. This is particularly advantageous when the arrangement has a plurality of receiving channels and associated conveyors, each for one file of the objects, inasmuch as the further advancement of any of the files can be interrupted when a jam occurs in that particular file, and the remaining conveyors may continue to advance their files of objects to their destinations.

It can happen, especially when the arrangement includes a plurality of the receiving channels and of the associated conveyors, each of the latter advancing a file of the objects, that other objects will be carried on the objects of these files in a "piggyback" fashion. To prevent these carried objects, which could cause a jam at a location downstream of the above-discussed part of the arrangement, from reaching this location, the arrangement of the present invention is preferably further provided with refuser means which is arranged at the downstream end of the receiving channel or channels. The refuser means may be stationary and merely retain the carried objects. However, experience has shown that it is particularly advantageous when, as proposed by the present invention, the refuser means includes a refuser element which includes a plurality of engaging portions and which is mounted for rotation in such a sense that the engaging portions travel opposite to the predetermined direction at and immediately upwardly of the downstream end of the receiving channel or channels. These rotating or orbiting engaging portions then engage the carried object and displace or throw the same back into the collection or onto the heap. The refuser means may further include at least one refuser cam which is arranged downstream of the refuser element.

So far, the arrangement of the present invention has been discussed only to the extent of its performance of a longitudinally aligning and conveying operation. As long as the objects are symmetrical with respect to a plane which is normal to the longitudinal axis of the respective object and halving the latter, this is all that is needed for achieving a proper orientation of the object since it is immaterial which one of two possible orientations the object assumes. However, when the objects are not symmetrical with respect to the normal plane, that is, when it matters which one of the two orientations the respective object assumes, it is advantageous, in accordance with an additional concept of the present invention, to equip the arrangement of the present invention with means for reversing those objects of the succession or file which have one of the two possible orientations, while maintaining the orientation of the remaining objects. This reversing means is situated downstream of the refuser means. By employing this reversing means, it is possible to achieve only a single orientation for all of the asymmetrical objects downstream of the reversing means.

Especially when the objects are asymmetrical as discussed above, they may have first portions which may enter second portions of the objects of the same file which are longitudinally aligned therewith. Under these circumstances, such objects would form undesired assemblies of objects that would create jams at the reversing means or elsewhere downstream of the refuser means. For this reason, the arrangement of the present invention further comprises means for disassembling such assemblies downstream of the refuser means, such disassembling means advantageously including two pairs of conveyors, the conveyors of each pair receiving the objects between themselves, the downstream pair of conveyors being advanced at a speed that exceeds that of the upstream pair of conveyors to advance the leading one of the objects of each of the assemblies more rapidly than the trailing one of the objects which is still engaged by the upstream pair of the conveyors, and to thus withdraw the first portion of one of such assembled objects from the second portion of the other of the assembled objects.

As to the aforementioned reversing means, it is to be mentioned that, in accordance with an aspect of the present invention, it preferably includes an abutment that extends into the trajectory of advancement of the objects (downstream of the downstream pair of conveyors) at a reversing location at which the respective object is free to descent by gravity, and at least one projection at each end of the reversing location and extending into the path of gravitational descent of a portion of a larger cross section of the respective object which has one of the two orientations, while a portion of a smaller cross section of another object which has the other of the two orientations clears or bypasses the same. This reversing means has a particularly simple construction.

After the objects have been properly oriented, it is necessary to deliver them into a dispensing hopper or to another destination. For this purpose, the arrangement of the present invention may include at least one of conveyors pair which entrain the individual objects between themselves and transport them into an intermediate storage that has an inclined bottom and an exit opening at the bottom of the incline, and another pair of conveyors which are spaced from each other by a distance exceeding the maximum transverse cross section of the objects and which transport the objects which have reached and passed through the exit opening of the intermediate storage after descending on the inclined bottom toward the dispensing hopper in at least two (but preferably more than two) files.

The novel features which are considered as characteristic of the invention are set forth in particular in the appended claims. The arrangement for orienting and conveying barrels of tampon inserters itself, however, both as to its construction and its mode of operation, together with additional features and advantages thereof, will be best understood upon persual of the following detailed description of certain specific embodiments with reference to the accompanying drawing.

BRIEF DESCRIPTION OF THE DRAWINGS

FIG. 4 is a top plan view of an initial part of an arrangement of the present invention;

FIG. 5 is a somewhat enlarged sectional view taken along the line V—V of FIG. 4;

FIG. 6 is a somewhat diagrammatic side elevational view of a second part of the arrangement of the present invention located downstream of the initial part illustrated in FIG. 4;

FIG. 7 is a view similar to that of FIG. 6 of but showing a third part of the arrangement of the present invention situated downstream of the second part;

FIG. 8 is a view of a fourth part of the arrangement of the present invention;

FIG. 9 is a top plan view of the arrangement of FIG. 8 with a barrel assuming one of two possible orientations;

FIG. 10 is a view similar to that of FIG. 9, but with the barrel in the other of two possible orientations;

DESCRIPTION OF THE PREFERRED EMBODIMENTS

Figure 1:
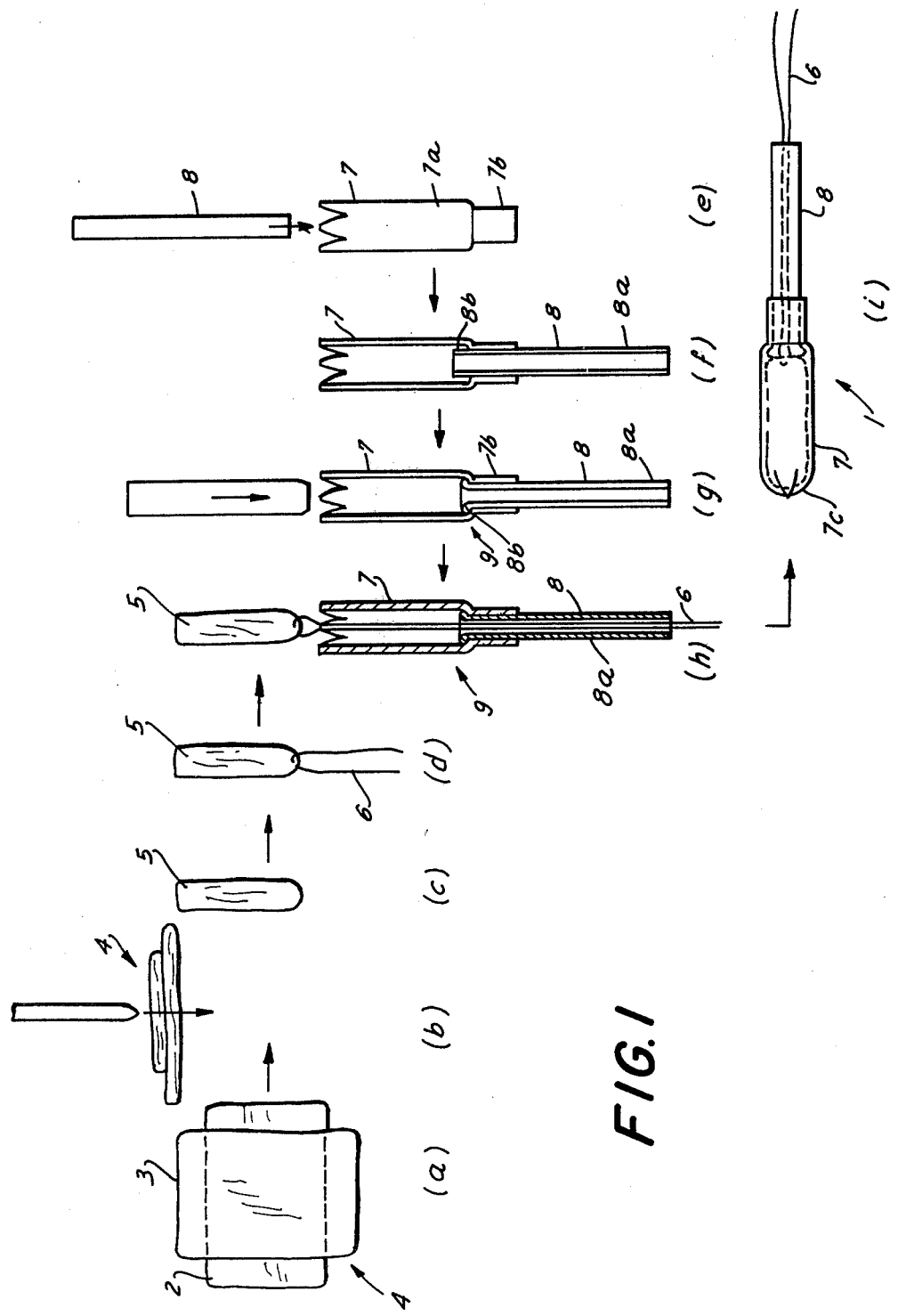
FIG. 1 is a diagrammatic representation of the steps which have to be performed in order to obtain a tampon inserter-catamenial tampon assembly.

Referring first to FIG. 1, it illustrates, in parts (a) to (i), a plurality of steps which are to be performed in a predetermined order to form a catamenial tampon-tampon inserter assembly 1 which is shown in its final form in part (i) of FIG. 1.

The assembly 1 is formed from a plurality of basic components, including two sections 2 and 3 of foraminous, preferably fibrous material, such as rayon. Such sections may be obtained by severing them from one or more continuous webs having the required dimensions. The sections 2 and 3 are superimposed upon one another in the manner illustrated in part (a) in top plan view, to form a cross-shaped formation 4. Thereafter, the formation 4 is deformed, in the manner indicated in part (b) of FIG. 1 in side elevational view, to form a body or tampon 5 shown in part (c). It will be appreciated that conversion of the formation 4 into the tampon 5 will involve the use of deforming tools. Preferably, the formation 4 is pushed into a confining sleeve in which it obtains its substantially cylindrical configuration.

In many instances, the tampon 5 must be cured after its formation, such as heated to a predetermined temperature and for a predetermined period of time, for instance, to reduce the moisture content thereof. This operation, if needed, is performed between the operations shown in parts (c) and (d) of FIG. 1, advantageously while the tampon 5 is confined in the aforementioned or another confining sleeve.

After the formation of the tampon 5, or after the curing thereof, a withdrawal string 6 is attached thereto. This operation, the result of which is indicated in part (d) of FIG. 1, is preferably performed while the tampon 5 is held in the illustrated vertical position, so that the two sections of the string 6 will hang, due to gravity forces, downwardly from the tampon 5.

The assembly 1 further includes a barrel 7 and a plunger 8 which together constitute a tampon inserter 9 in their assembled condition. The barrel 7 and the plunger 8 are supplied from different sources or storage arrangements to an assembling location, such as that shown in part (e) of FIG. 1. Prior to the delivery of the barrels 7 to the assembling location, they may have to be reoriented so that each thereof assumes the position illustrated in part (e).

As shown, the respective barrel 7 has a larger-diameter main portion 7a, and a smaller-diameter end portion 7b. The plunger 8, as shown, is tubular and cylindrical when it reaches the assembling location. Thereat, it is introduced into the interior of the barrel 7 through the main portion 7a thereof, and into, and possibly to a certain extent but not entirely beyond, the end portion 7b. This is illustrated in part (f) of FIG. 1, where the reference numeral 8a denotes that portion of the plunger 8 which extends outwardly of the end portion 7b of the barrel 7.

After the assembly of the plunger 8 with the barrel 7, that end 8b of the plunger 7 which is still received in the main portion 7a of the barrel 7 is flared, as indicated in part (g) of FIG. 1. Of course, the plunger 8 could be delivered to the assembling location already in its flared condition; however, experience has shown that the flaring of the end of the plunger 8 only after its assembly with the barrel 7 is advantageous in that the plunger 8 can be delivered to the assembling location in any of two orientations; this dispenses with the otherwise existing need for taking measures aimed at assuring that the plunger 8 is supplied to the assembling station in one of these orientations. The flaring of the end 8b of the plunger 8 results in a situation where the flared end 8b engages behind a shoulder which forms the transition between the main portion 7a and the end portion 7b of the barrel 7 and thus prevents the plunger 8 from continuing its movement in the direction of introduction into the barrel 7 through the end portion 7b and to the exterior of the barrel 7. Of course, the flared end portion 8b does not prevent the plunger 8 from being expelled from the barrel 7 in a direction opposite to its introduction; however, this is not disadvantageous during the assembling operation since neither the barrel 7 nor the plunger 8 are subjected to any forces which would cause them to move relative to one another in the aforesaid opposite direction so as to expel the plunger 8 from the barrel 7 through the main portion 7a of the barrel 7. On the other hand, the movement of the plunger 8 relative to the barrel 7 in this direction is needed for expulsion of the tampon 5 from the barrel 7 of the tampon inserter 9 when the latter is used.

The assembled inserter 9 and the tampon 5 provided with the withdrawing string 6 are brought together at an inserting station substantially in the positions shown in part (h) of FIG. 1. This means that, if either the tampon 5 is formed, or the tampon inserter 9 is assembled, in any other orientation than that shown, it will have to be reoriented or turned before it reaches the inserting station. At this station, both the tampon 5 and the inserter 9 are substantially vertical, the inserter 9 being located underneath the tampon 5 with its barrel 7 being situated at a higher elevation than its plunger 8. The string 6 extends downwardly from the lower end portion of the tampon 5 to which it is attached and, as shown in part (h) of FIG. 1, it is introduced into and passes through the tampon inserter 9, preferably beyond the portion 8a of the plunger 8. The string 6 can be introduced into the tampon inserter 9, for instance, by applying subatmospheric pressure to the lower end of the plunger 8 so that the string 6 is pulled into the tampon inserter 7 by suction.

When the string 6 is fully accommodated in the inserter 9, the tampon 5 is introduced into the interior of the main portion 7a of the barrel 7, such as by being pushed from above into the barrel 7. Advantageously, if the string 6 is pulled into the tampon inserter 7 by suction, the subatmospheric pressure at the lower end of the plunger 8 is continued while the tampon 5 is being introduced into the barrel 7. This not only causes the string 6 to continue its movement in a substantially taut condition and without tangling toward, into and beyond the plunger 8, but also aids in the introduction of the tampon 5 into the barrel 7 by creating a pressure differential between the two ends of the tampon 5 which acts in the direction of introduction of the tampon 5 into the barrel 7.

Once the tampon 5 is fully accommodated in the interior of the main portion 7a of the barrel 7, an end portion 7c which is situated longitudinally opposite the smaller-diameter end portion 7b of the barrel 7 is closed. To this end, this end protion 7c is originally provided with serrations which are so shaped that, once they are bent to a substantially hemispherical shape as shown in part (i) of FIG. 1, they will substantially complement one another without leaving any, or by leaving only small, slots therebetween. At least the barrel 7 is made of a thermosplastic or thermosetting synthetic plastic material, and a permanent deformation of the serrations into their final positions is achieved by simultaneously subjecting them to heat and deforming pressure. Of course, the serrations forming the end 7c of the barrel 7 must remain flexible enough to permit them to yield during use of the tampon inserter 7, i.e., to move out of the way of the tampon 5 which is being ejected from the barrel 7 by displacing the plunger 8 relative to the barrel 7 in a direction opposite to that of the original introduction thereof into the barrel 7.

Figure 2:
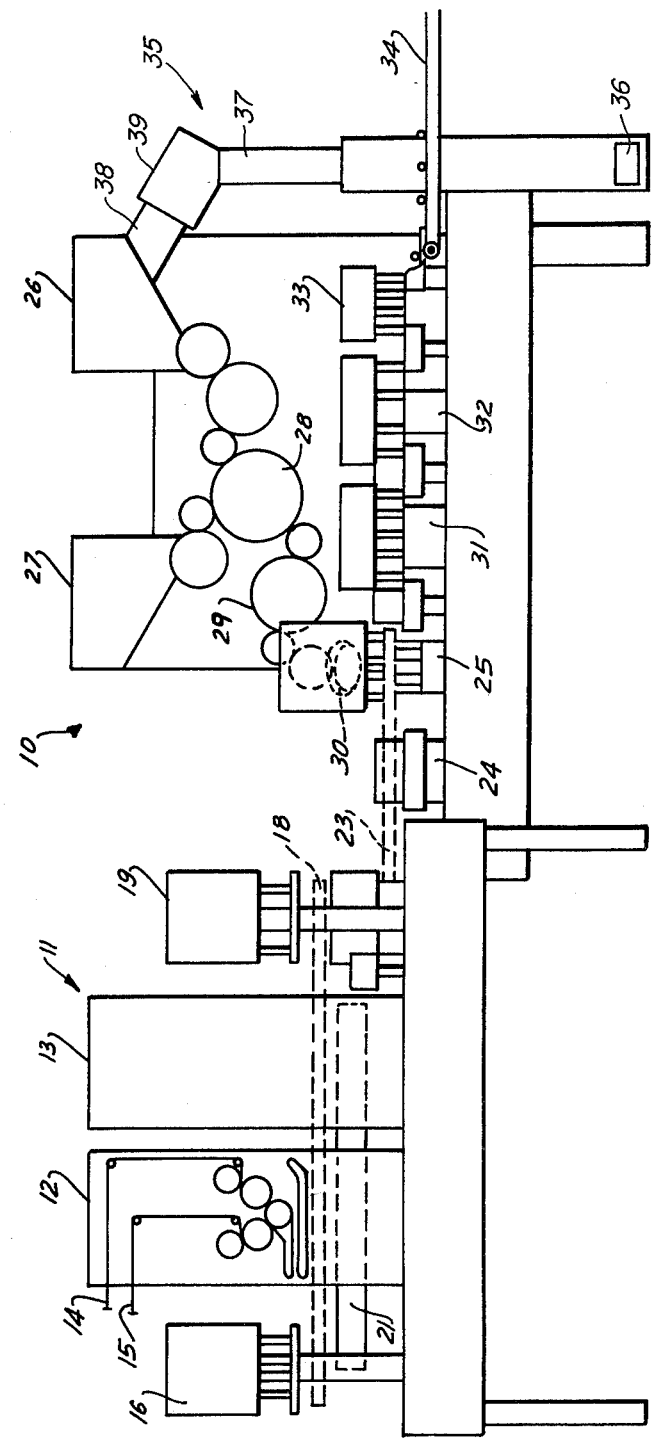
FIG. 2 is a side elevational view of an apparatus capable of performing the steps which have been indicated in FIG. 1 and including the arrangement of the present invention.
Figure 3:
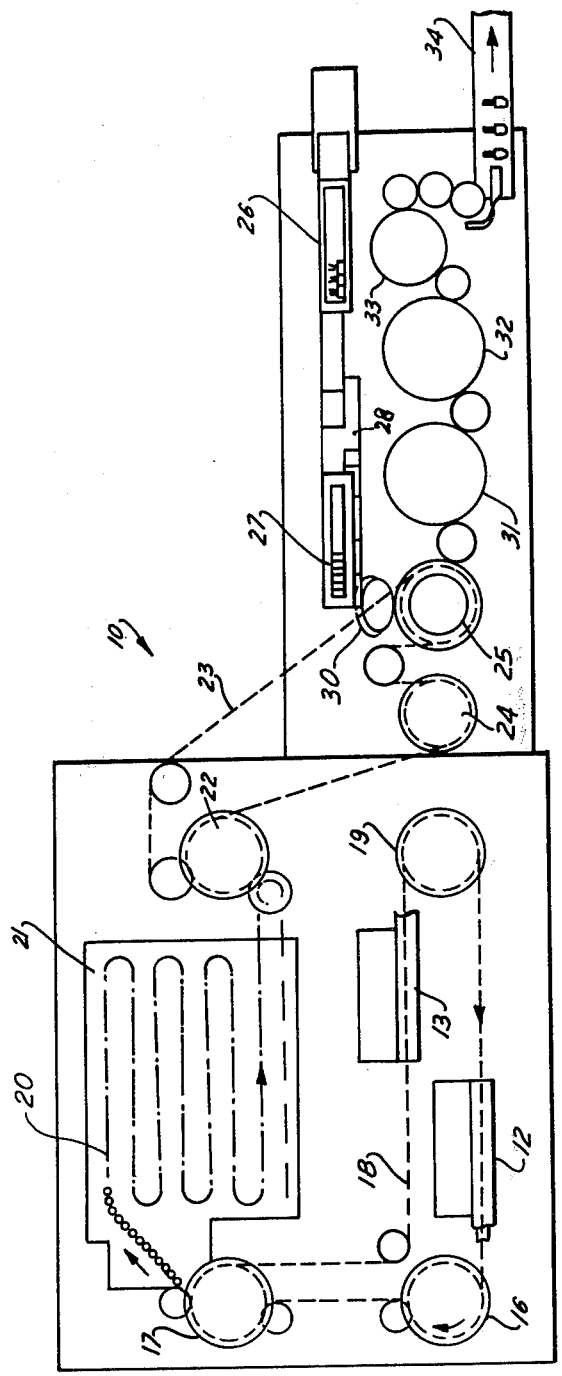
FIG. 3 is a top plan view of the apparatus of FIG. 2.

A machine 10 which is capable of performing all of the above-mentioned operations and more and in which the present invention is embodied is shown, in a simplified manner, in FIGS. 2 and 3. This machine 10 includes a cutting arrangement 11 consisting of two cutting towers 12 and 13. As shown, the cutting tower 12 is supplied with two webs 14 and 15. The same is true about the cutting tower 13; however, particularly in view of the fact that the latter is identical or at least similar to the cutting tower 12, no details of the same have been shown in the drawing in order not to unduly encumber the same.

Each of the cutting towers 12 and 13 cuts individual sections 2, 3 from the webs 14 and 15 (and the corresponding webs supplied to the cutting tower 13) and superimposes the same upon one another to form assemblies 4 in the manner indicated in FIG. 1. At the deforming station 16, the assemblies 4 issuing from the tower 12 are deformed, in succession, into the tampons 5. From there, the tampons 5 travel to a transfer station 17. An endless conveyor 18, preferably a chain, transports the tampons 5 between the stations 16 and 17. The cutting tower 13 operates in the same manner, but the assemblies 4 formed thereat are supplied to another deforming station 19 where the assemblies 4 are converted into a further succession of tampons 5 and transferred to the same conveyor 18. The operation of the cutting towers 12 and 13 is so synchronized that the tampons 5 formed at the deforming station 16 will alternate with those formed at the deforming station 19.

At the transfer station 17, the tampons 5 are transferred to another conveyor 20 which transports the tampons 5 through a curing oven 21. As shown, the conveyor 20 advances the tampons 5 in a multiple-hairpin-shaped trajectory through the curing oven 21. The conveyor 20 delivers the tampons 5 to another transfer station 22 where the cured tampons 5 are transferred to a further conveyor 23 which transports the tampons 5 to a string-attaching station 24 where a string 6 is attached to each tampon 5. From here, the conveyor 23 advances the tampons 5 to an assembling station 25 where the tampons 5 are assembled with the tampon inserters 9.

Referring now particularly to FIG. 2, it may be seen that the apparatus 10 further includes two storage hoppers 26 and 27. The hopper 26 accommodates a supply or properly oriented barrels 7, and the hopper 27 accommodates a supply of plungers 8 each of which assumes one of two permissible orientations. The barrels 7, on the one hand, and the plungers 8, on the other hand, are paid out of the respective storage hoppers onto a series of transporting rollers which eventually bring the barrels 7 and the plungers 8 together in substantial axial alignment with one another on an inserting drum 28. The barrels 7 and the plungers 8 are assembled with one another at respective inserting locations of the inserting drum 28. The assemblies of the barrels 7 and plungers 8 are then transferred, in succession, to a flaring drum 29 where the end portions 8b of the plungers 8 are flared in the manner and for the purpose discussed above.

It will be noted that the conveyor 23 brings the tampons 5 to the assembling station 25 in their proper vertical orientation, that is, with the string 6 hanging downwardly from the lower end portion of the tampon 5. On the other hand, upstream of the assembling station 25, the barrels 7 and the plungers 8 and eventually their assemblies or the tampon inserters 9 are being conveyed in substantially horizontal positions as far as their longitudinal axes are concerned. Hence, the tampon inserters 9 have to be reoriented prior to their feeding into the assembling station 25. To this end, there is provided a transfer disk 30 which rotates about an axis substantially halving the angle between the planes along which the tampons 5, on the one hand, and the tampon inserters 9, on the other hand, move. The tampon inserters 9 are transferred, downstream of the flaring drum 29, to the transfer disk 30 and their orientation is changed to correspond to that of the tampons 5, during the orbiting thereof on the transfer disk 30 about the aforementioned inclined axis.

During the travel through the assembling station 25, the tampons 5 are introduced into the barrels 7 of the consecutive tampon inserters 9 in the manner which has been discussed before. Then, the tampon inserters 9, with the tampons 5 properly accommodated therein, are transferred to a heating drum 31 wherein heat and pressure are applied to the serrated end portions 7c of the barrels 7 to deform and close the same. Advantageously, the closed tampon inserters 9 are then transferred to a cooling drum 32 wherein the previously heated end portions 7c of the barrels 7 of the tampon inserters 9 are cooled to remove the heat accumulated in such end portions 7c and to cause them to lose their heat-induced plasticity. The closing of the end portion 7c of the barrel 7 converts the intermediate assembly of the tampon 5 with the tampon inserter 9 into the final tampon-tampon inserter assembly 1.

It is further advantageous when, after leaving the cooling drum 32, the assemblies 1 are passed through another station 33 where they may be tested, for instance, for proper closing of the end portion 7c, for the presence of the string 6 and its extension outwardly of the plunger 8, or for other parameters or features, or where, for instance, a minute quantity of perfume may be injected into the assembly 1 and onto the tampon 5 accommodated therein, if such operations have not already been performed upstream of this station 33. After leaving the station 33, the assemblies 1 are reoriented so as to extend substantially horizontally and, in this position, they are discharged onto a final conveyor 34, such as a conveyor belt, which carries them out of the machine or apparatus 10, for instance, to a packing location or the like.

The reference numeral 35 in FIG. 2 denotes a downstream part of a feeding arrangement by means of which properly oriented barrels 7 are fed into the barrel storage hopper 26. To reach the storage hopper 26 in a proper orientation (in the proper one of the two abovementioned two possible orientations), the barrels 7 must already be properly oriented when they enter an inlet opening 36 of the feeding part 35 which includes a lower portion 37 in which the axes of the barrels 7 extend in parallelism with one plane, an upper portion 38 in which the axes of the barrels 7 extend in parallelism with a second plane substantially normal to the first plane, and an intermediate portion 39 in which the barrels are turned about a vertical axis from parallelism with the first plane into parallelism with the second plane. Preferably, the barrels 7 are advanced through the feeding part 35 in more than one file, such as several abreast. FIGS. 4–12 illustrate that part of the arrangement of the present invention which is operative for "unscrambling" the barrels 7 which are originally delivered to the machine in a random orientation, that is, to give them the desired orientation, and for conveying such barrels 7 toward the inlet opening 36 of the feeding part 35. FIGS. 4 and 5 show an initial or upstream part of this arrangement. At this location, the arrangement includes a plurality of alternating rollers 40 and 41 which are rotated by a conventional drive which has been omitted from the drawing for the sake of clarity, in opposite senses, as indicated by arrows 42 and 43. Neighboring rollers 40 and 41 cooperate with one another and define with each other receiving channels 44 for the barrels 7.

When a barrel 7 of a layer or pile of barrels 7 resting on the rollers 40 and 41 happens to initially assume one of two possible orientations in which its axis is parallel to those of the rollers 40, 41, it will immediately fall into the respective receiving channel 44. On the other hand, when the barrel 7 has any other orientation, it will rest on at least one of the rollers 40 and 41, but more likely on both, and the rotation of the rollers 40 and 41 in opposite senses will rotate such barrel in the clockwise or counter-clockwise direction as seen in FIG. 4, until this barrel 7 becomes parallel to the axes of the rollers 40 and 41 and enters the respective receiving channel 44.

The upper run of a discrete conveyor 45 is accommodated in each channel 44 and advances longitudinally thereof in the direction of an arrow 46. This upper run is so positioned between the rollers 40 and 41 that, when the barrel 7 enters the respective channel 44, it will rest on this upper run of the conveyor 45 and will be entrained thereby for advancement therewith from below the layer, pile or heap of barrels 7 in the direction of the arrow 46. Preferably, when the barrels 7 rest on the conveyor 45, a clearance exists between the same and at least one of the rollers 40, 41 so that the latter will not retard the advancement of the barrels 7 with the upper run of the conveyor belt 45. Advantageously, each conveyor belt 45 is constructed as a V-belt.

FIG. 4 also shows that it may happen that the smaller diameter end portion 7a of one of the barrels 7 enters the larger diameter end portion 7b of another barrel 7. In the absence of any measures remedying the situation, a jam could occur downstream of the first part of the arrangement that is illustrated in FIGS. 4 and 5. However, such jam could occur also for other reasons or it may be desired to discontinue, for one reason or another, the advancement of the barrels 7 through at least one of the receiving channels 44. To be able to do so, the arrangement includes at least one, but preferably two, plate-shaped lifting movement interrupting elements 47 which are movable, in a conventional manner, in the direction of the double-headed arrow 48. The lifting elements 47 are arranged between the upper run of each belt conveyor 45 and the respective rollers 40 and 41; in their retracted positions illustrated in FIG. 5, they do not interfere with the advancement of the barrels 7 with the upper run of the respective conveyor 45. However, once they are displaced upwardly, they will lift the barrel or barrels 7 then present in the respective receiving channel 44 out of the upper run of the corresponding conveyor 45 so that such barrel or barrels 7 will become stationary, while the conveyor 45 may continue its movement. This is particularly advantageous when the advancement of the barrels 7 through at least one, but not all of the receiving channels 44 to be discontinued.

Now, it can happen that additional barrels 7 are carried on top of the barrels 7 which are partially received in the receiving channels 44, in a "piggyback" fashion as illustrated in FIG. 6. Further advancement of such carried barrels would cause trouble downstream of the arrangement illustrated in FIG. 4. Hence, the arrangement of the present invention is equipped with a first refuser 49 having a plurality of engaging portions 50 and rotated, in a conventional manner, in the direction indicated by an arrow 51. As the carried barrel 7 approaches the first refuser 49, one or the other of the engaging portions 50 will invariably engage the same and throw it back onto the pile or heap of the barrels. However, it could also happen that additional barrels 7 could be carried intermediate the barrels of the two piles emerging from the channels 44, in which case they would not extend upwardly enough to be engaged by the engaging portions 50. Thus, the arrangement of the present invention is further equipped with second refuser means 52 which includes a plurality of cam-shaped elements 63 rotating in the direction of an arrow 54 and extending, at least in some positions thereof, into the spaces between the barrels 7 emerging from the individual receiving channels 44 and supported on a first conveyor 55. These cam-shaped refuser elements 53 will again return the improperly positioned barrels 7 towards the receiving channels 44. As can be seen in FIG. 7, the upper run of the conveyor 55 which carries the barrels 7 is juxtaposed at a region situated downstream of the second refuser 52 with the lower run of another conveyor 56 and forms therewith a pair of cooperating conveyors. Another pair of similarly cooperating conveyors 57 and 58 is arranged downstream of this first pair of conveyors 55 and 56. The upper and lower runs of the respective conveyors 55 and 56, on the one hand, and of the conveyors 57 and 58, on the other hand, confine the barrels 7 between themselves. Now, the speed of advancement of the downstream conveyors 57 and 58 exceeds that of the upstream conveyors 55 and 56, but the speed of advancement of the cooperating runs of each of the conveyor pairs 55, 56 and 57, 58 is substantially the same. No matter which one of the two possible orientations those barrels 7 which are partially received within one another assume, the downstream pairs of conveyors 57, 58 will engage the leading one of these barrels and advance the same at the higher speed, while the trailing one of these barrels is still engaged by the upstream pair of conveyors 55, 56 and advanced thereby at the lower speed. In this manner, the previously interengaged barrels 7 are disassociated from one another.

At the downstream ends of the conveyors 57 and 58, the barrels 7 of each file or succession of barrels 7 are discharged onto a platform 59 shown in FIG. 8 and continue their movement in sliding engagement with the platform 59 and further across a space 60 until one of the ends of the respective barrels 7 reaches an abutment 61 arranged across the space 60 from the platform 59, and is stopped thereby. At this point, the pull of gravity will attempt to displace the respective barrel downwardly into an internal compartment 62 of a funnel-shaped member 63. Projections 64 and 65, here illustrated as circular pins, extend into the internal compartment 62 below and close to the platform 59, one the one hand, and the abutment 61, on the other hand. Now, the barrels 7 may arrive to the abutment 61 in one of the two possible orientations, as illustrated in FIGS. 9 and 10, respectively. In each of these instances, one of the pairs of projections 64 or 65 will engage and retain the larger-diameter end portion 7a of the respective barrel 7, while the smaller-diameter end portion 7b of this barrel 7 will bypass the other pair of projections 65 or 64. In this manner, it is assured that each barrel 7 will invariably leave the internal compartment 62 in the position illustrated in FIG. 8, that is, with the smaller diameter end portion 7b first.

Figure 11:
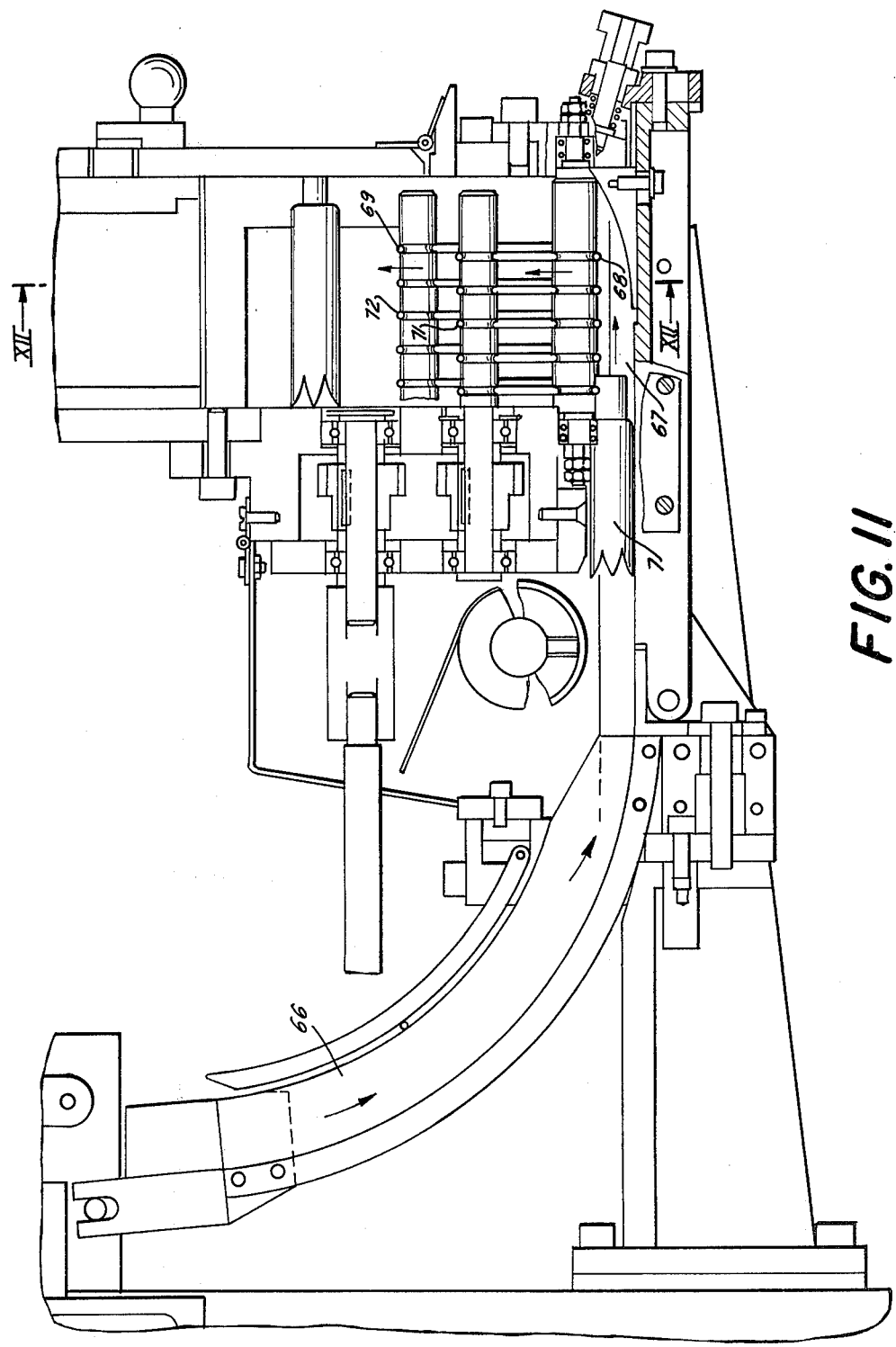
FIG. 11 is a detailed side elevational view of a fifth part of the arrangement of the present invention located downstream of the fourth part illustrated in FIG. 8.

The properly oriented barrel 7 then enters a vertical chute 66 the continuation of which is illustrated in FIG. 11. At its lower end, the chute 66 is curved so that it eventually extends substantially horizontally. The properly oriented barrels 7 slide down the chute 66 and along the curved lower end portion of the latter until they reach an engaging region 67 where they come to a stop. At the engaging region 67, an oncoming barrel 7 is engaged by a pair of conveyors 68 and 69 (compare FIG. 12) and is conveyed thereby in the upward direction and into the respective channel 70. As illustrated in FIG. 11, each of the conveyors 68, 69 includes a plurality of adjacent but spaced conveyor elements 71, 72 which are preferably O-shaped in cross section.

Figure 12:
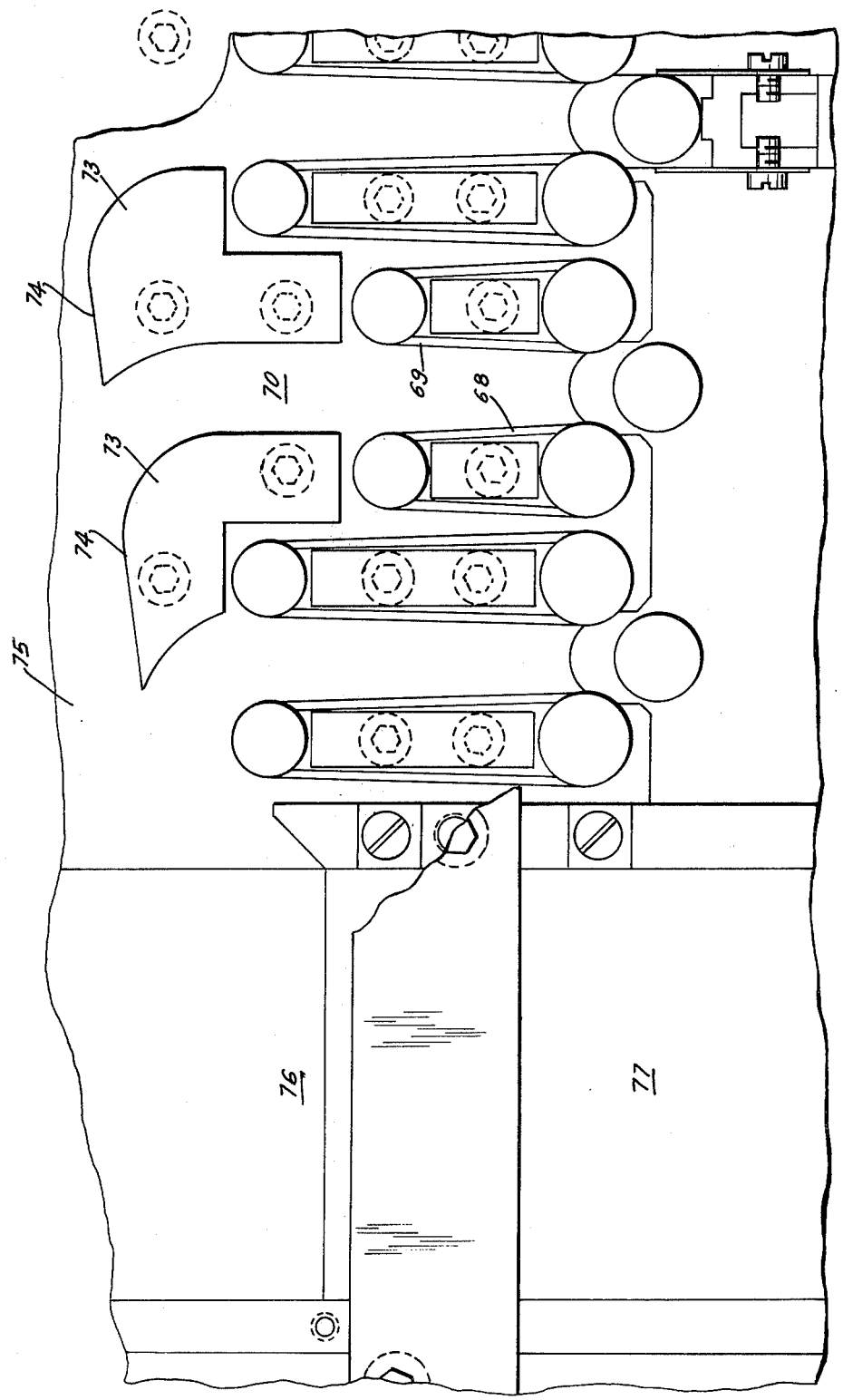
FIG. 12 is a somewhat diagrammatic sectional view taken along the line XII—XII of FIG. 11.

As can be seen in FIG. 12, each channel 70 extends between guiding elements 73 each of which has a sloping upper surface 74. The sloping surfaces 74 constitute the sloping bottom of an intermediate storage space 75. The surfaces 74 slope downwardly toward an exit opening 76 from which a guiding channel 77 leads to the inlet opening 36 of the feeding part 35 which is shown in FIG. 2. The barrels 7 which emerge from the channel 70 gradually roll down the inclined bottom of the space 75, which bottom is constituted by the surfaces 74, until it reaches the exit opening 76 and passes through the same into the channel 77. The dimensions of the channel 77 are such that it can accommodate several of the barrels next to one another for joint travel toward the inlet opening 36.

It may be seen from the above discussion of the arrangement of the present invention that it is very simple, renders it possible to achieve a proper orientation of the barrels 7, reduces to a minimum, if not eliminates, the possibility of jamming, renders it possible to partially or fully discontinue the delivery of the barrels 7 in the event of a jam without any need for discontinuing the operation of the conveyors 45 or any components arranged downstream thereof, and provides a sufficient supply of the barrels 7 to the inlet opening 36 even if the operation of one or more of the conveyors 45 is discontinued, particularly due to the accumulation of the barrels 7 in the space 75 or in the channel 77 during normal operation of all of the conveyors 45.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the claims.

We claim:

1. An arrangement for orienting and conveying elongated objects, especially barrels of tampon inserters, comprising means for supporting a collection of randomly oriented elongated objects, including at least one pair of substantially parallel support elements including a first and a neighboring second element, said first support element including a cylindrical engaging surface having a longitudinal axis and being mounted for rotation about such axis, said support elements being spaced apart as considered transversely of said axis to define a receiving channel for a succession of objects which are oriented in parallelism with said axis; means for rotating said first support element about said axis whereby said engaging surface of said first element frictionally engages any improperly oriented objects supported by said elements and effects reorientation of improperly oriented objects into parallelism with said axis and entry into said receiving channel; conveyor means extending into said channel and advancing in a predetermined direction along said axis to entrain the objects which are received in said channel; and means for interrupting the movement of objects with said conveyor means, including at least one lifting element mounted on said supporting means for movement between a retracted position in which it is spaced from the objects received in said channel and an extended position in which it lifts the objects out of the range of said conveyor means.

2. The arrangement as defined in claim 1, wherein said second support element is mounted for rotation about the respective longitudinal axis.

3. The arrangement as defined in claim 2; further comprising means for rotating said second support element about the respective longitudinal axis.

4. The arrangement as defined in claim 3, wherein said rotating means for said first support element rotates the latter in a first direction, and the rotating means for said second support element rotates the latter in the opposite direction.

5. The arrangement as defined in claim 1, wherein said supporting means includes at least one additional support element similar to said first and second support elements and adjacent to and substantially parallel with one of said first and second support elements, said additional element and said one element constituting an additional pair of support elements and defining an additional receiving channel for an additional succession of properly oriented objects.

6. The arrangement as defined in claim 1, wherein said conveyor means includes at least one belt conveyor having an upper run extending longitudinally of said receiving channel to engage from below the objects in said channel.

7. The arrangement as defined in claim 1, wherein said one lifting element is received between one of said support elements and said conveyor means in said extended position and said movement interrupting means further includes another lifting element similar to and movable together with said one lifting element and received between said conveyor means and the other of said support elements in the extended position thereof.

8. The arrangement as defined in claim 1, further comprising refuser means arranged at the downstream end of said receiving channel and operative for preventing objects resting on and carried by the succession of objects from advancing beyond said downstream end.

9. The arrangement as defined in claim 8, wherein said refuser means includes a refuser element having a plurality of object engaging portions and mounted for rotation in a direction to move said engaging portions counter to said predetermined direction immediately upwardly of said downstream end to engage the carried objects and return the engaged objects back into the collection.

10. The arrangement as defined in claim 9, wherein said refuser means further includes a refuser cam downstream of said refuser element.

11. The arrangement as defined in claim 8 for orienting elongated objects having first portions capable of entering second portions of other objects which are longitudinally aligned therewith to form undesired assemblies, further comprising means for separating the assemblies downstream of said refuser means, including an upstream pair and a downstream pair of conveyors, the conveyors of each pair receiving the objects between themselves and the downstream pair or conveyors moving at a speed exceeding that of the upstream pair of conveyors to advance the leading one of the objects of each of the assemblies more rapidly than the trailing object which is still moved by said upstream pair of conveyors and to thus withdraw the first portion of one of such objects from the second portion of the other object.

12. The arrangement as defined in claim 8 for orienting elongated objects having a changing cross section in the longitudinal direction, further comprising reversing means situated downstream of said refuser means and operative for reversing those objects of the succession which have one of two possible orientations, while maintaining the orientation of the remaining objects.

13. The arrangement as defined in claim 12, wherein said reversing means includes an abutment extending into the trajectory of advancement of the objects at a reversing location where the objects are free to descend by gravity, and at least one projection at each end of the reversing location and extending into the path of gravitational descent of a portion of a larger cross section of the respective object having one of said two orientations, while a portion of a smaller cross section of the respective object having the other of the two orientations clears the same.

14. The arrangement as defined in claim 12, further comprising a hopper, an intermediate storage and means for delivering properly oriented objects into said hopper, including at least one first pair of conveyors for entraining discrete objects and for transporting such objects into said intermediate storage, said storage having an inclined bottom and an exit opening at the bottom of the incline, and further comprising a second pair of conveyors spaced from each other by a distance exceeding the maximum transverse dimension of an object and arranged to transport the objects which have reached and passed through the exit opening of said intermediate storage, after descending on the inclined bottom, toward said hopper in at least two files.

* * * * *